United States Patent [19]

Yung

[11] Patent Number: 4,697,605
[45] Date of Patent: Oct. 6, 1987

[54] CONTACT LENS CLEANING APPARATUS

[75] Inventor: Simon K. C. Yung, Jardines Lookout, Hong Kong

[73] Assignee: SMC Metal Tech Co., Ltd., Hong Kong

[21] Appl. No.: 869,417

[22] Filed: Jun. 2, 1986

Related U.S. Application Data

[63] Continuation-in-part of Ser. No. 676,004, Nov. 29, 1984, Pat. No. 4,607,652.

[30] Foreign Application Priority Data

Aug. 6, 1985 [EP] European Pat. Off. .......... 85304482

[51] Int. Cl.⁴ .............................................. B08B 3/12
[52] U.S. Cl. .................. 134/107; 134/184; 310/316; 366/127
[58] Field of Search ................... 134/1, 184, 107; 366/127; 310/316

[56] References Cited

U.S. PATENT DOCUMENTS

| | | | |
|---|---|---|---|
| 2,814,575 | 11/1957 | Lange et al. ............... | 134/1 |
| 2,970,073 | 1/1961 | Prange ...................... | 134/1 |
| 2,994,330 | 8/1961 | Catlin et al. ............... | 134/58 R |
| 3,007,478 | 11/1961 | Leonhardt et al. ......... | 134/57 R |
| 3,033,710 | 5/1962 | Hightower et al. ........ | 134/1 |
| 3,034,520 | 5/1962 | Jewell ....................... | 134/99 |
| 3,278,770 | 10/1966 | Shoh ......................... | 310/316 |
| 3,291,640 | 12/1966 | Livingston ................. | 134/1 |
| 3,371,233 | 2/1968 | Cook .......................... | 134/184 X |
| 3,402,075 | 9/1968 | Goldwasser et al. ...... | 134/1 |
| 3,403,245 | 9/1968 | Eaton ........................ | 219/494 |
| 3,481,687 | 12/1969 | Fishman . | |
| 3,516,861 | 6/1970 | Menkes et al. ............ | 134/1 |
| 3,640,295 | 2/1972 | Peterson ................... | 134/159 |
| 3,672,823 | 6/1972 | Boucher . | |
| 3,697,222 | 10/1972 | Sierra . | |
| 3,708,263 | 2/1973 | Boucher . | |
| 3,720,402 | 3/1973 | Cummins et al. .......... | 134/184 X |
| 3,742,492 | 6/1973 | Proctor ..................... | 310/316 X |
| 3,771,772 | 11/1973 | Honda ....................... | 366/127 X |
| 3,866,068 | 2/1975 | Krenicki et al. ........... | 310/316 |
| 3,871,395 | 3/1975 | Murry ....................... | 134/184 X |
| 3,912,450 | 10/1975 | Boucher . | |
| 3,990,906 | 11/1976 | Johnston et al. .......... | 134/1 |
| 4,211,744 | 7/1980 | Boucher .................... | 422/20 |
| 4,271,317 | 6/1981 | Furnichi et al. ........... | 310/316 |
| 4,382,824 | 5/1983 | Halleck ..................... | 134/1 |

FOREIGN PATENT DOCUMENTS 947699 1/1964 United Kingdom .

Primary Examiner—Philip R. Coe
Attorney, Agent, or Firm—Lyon & Lyon

[57] ABSTRACT

A contact lens cleaning and disinfecting apparatus with a cavity (14) in which a contact lens is to be cleaned by an aqueous non-chemosterilant liquid such as a saline solution. An ultra-sonic transducer (20) applies vibrations to the cavity (14). The oscillator driving the transducer includes a transformer feedback circuit using one or more cores of high magnetic permeability and low core loss to give a stable resonant frequency. A timer (34) may be driven from this resonant frequency. In one embodiment the cavity (14) and the sealing cap (16) may be removable together with the transducer (20) from the rest of the housing of the apparatus so that lenses can be transported conveniently after cleaning and before use. According to another embodiment the waste heat from power transistors (Q2, Q3) can be used to heat the cleaning liquid in the cavity.

7 Claims, 6 Drawing Figures

CONTACT LENS CLEANING APPARATUS

This application is a continuation-in-part of, application Ser. No. 676,004, filed Nov. 29, 1984, and now U.S. Pat. No. 4,607,652.

BACKGROUND OF THE INVENTION

This invention relates to the cleaning and disinfecting of contact lenses. In particular the invention relates to apparatus in which the cleaning and disinfecting of the lenses is effected by immersing the lenses in a non-chemosterilant aqueous fluid and subjecting the lenses to ultrasonic vibrations.

To avoid eye infections and irritation it is highly desirable that contact lenses be thoroughly cleaned and disinfected at regular intervals. Some systems have proposed immersing the lenses in a cleaning or disinfecting liquid and also heating the liquid. Such systems have not provide very satisfactory in practice.

It has also been proposed to use ultrasonic vibrations to assist the cleansing but the apparatus used has generally been rather bulky and complicated. Usually it has been proposed that in a first step the lens should be subjected to ultra-sonic vibration to loosen impurities and then in second step the lens be disinfected by heating in a chemical disinfecting solution. The heating in the solution results in promoting coagulation of a coating on the lens which reduces its transparency with time.

It is therefore an object of the invention to provide an improved and relatively simple and portable apparatus for conducting this type of cleaning and disinfecting of contact lenses without the need to use chemosterilants.

SUMMARY OF THE INVENTION

According to the invention there is provided a contact lens cleaning and disinfecting apparatus, comprising at least one cavity for containing at least one contact lens together with an aqueous non-chemosterilant liquid, at least one ultrasonic transducer for applying ultrasonic vibrations to the liquid and lens contained in the cavity, oscillating means for driving the ultrasonic transducer including a transformer feedback circuit using one or more cores of high magnetic permeability and low core loss to stabilize the resonant frequency of the ultrasonic transducer means, and a timer for controlling the energizing of the oscillator means for a predetermined period of time.

Such apparatus operates relatively efficiently and so can use as its power supply a simple DC battery supply. It does not therefore require to use a mains supply. The efficiency of the operation is promoted by the use of the transformer feedback circuit, an example of which is a dual ferrite core transformer feedback circuit. The apparatus can therefore be quite compact and can be readily portable.

Also the use of the transformer feedback circuit ensures a relatively steady resonant frequency for the ultrasonic transducer irrespective of the variations in the amount of and/or the size and type of lens in the cavity. Further variations in the type of liquid, the supply voltage and the temperature also largely do not affect the resonant frequency. Because of this the resonant frequency will always be substantially constant and so the time of operation of the apparatus can be controlled by a simple electrical timer without need of any compensating adjustments. Thus the timer can be a simple crystal controlled timer circuit.

Alternatively the resonant frequency will be sufficiently constant for that frequency to be used to drive the operation of an associated timer which can be used to predetermine the period of operation.

According to one embodiment no separate heating of the fluid during the application of the ultra-sonic energy is provided, and the fluid and lens will heat up from room temperatures to about 65° C. in 15 to 20 minutes and so the time of operation should be at least 25 minutes and preferably from 30 to 40 minutes. However, according to one preferred embodiment, the liquid can be heated using the waste heat available from one or more power transistors used to drive the transducer. This can very simply be achieved by conducting heat to the cavity from these transistors by heat conducting means such as a strip of metal contacting the outer wall of the cavity and in contact with the transistors. This has important advantages in saving energy since the time of operation can be reduced.

According to other embodiments, the time of operation can be kept relatively short, e.g. 10 to 15 minutes, and the temperatures of the liquid need not exceed 35° C. Heating of the liquid using the waste heat from the power transistors can still optionally be employed.

The apparatus is very effective is disinfecting lenses because the frequency of the vibrations in the cavity is resonant and largely constant which has been found to promote the killing and removal of bacteria. Preferred frequencies of oscillation should be in the range of 35 to 40 KHz.

The apparatus of the invention uses a simple saline solution of a type which is widely available. No special solution or fluid is required. Thus no chemical disinfectants are necessary, which has important advantages of avoiding the risk of introducing into the eye chemicals which could be dangerous or unpleasant or to which the user may be allergic. This is in contrast with some prior types of apparatus which have merely used heat to sterilize the lens which may coagulate and so deteriorate the lens coating because of the long heating time required or have merely used chemicals to sterilize the lens without the cleaning effect of the ultrasonic vibrations.

An important advantage of the invention is that the lens are cleaned and disinfected in one step. The apparatus is therefore simple to use.

A preferred embodiment of the apparatus for cleansing and disinfecting contact lenses according to the invention will now be described, by way of example, with reference to the accompanying drawings.

DETAILED DESCRIPTION OF THE PREFERRED EMBODIMENT

Figure 1:
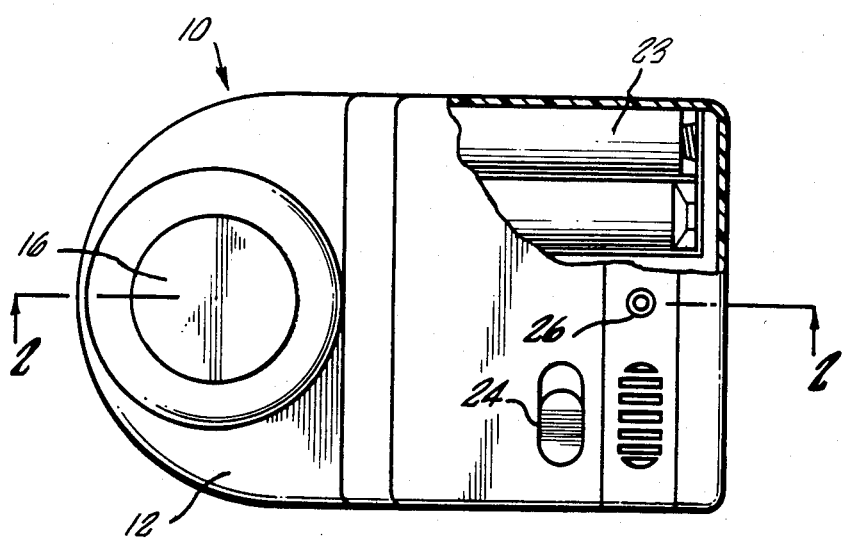
FIG. 1 is a broken-away plan view of the apparatus.
Figure 2:
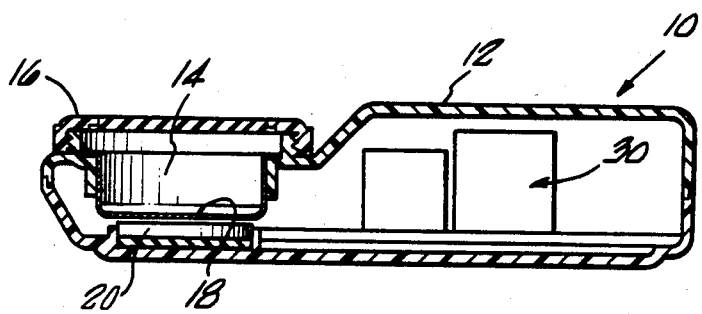
FIG. 2 is a section taken along the line 2—2 of FIG. 1.

The apparatus 10 comprises a housing 12 in which is formed a cavity 14. This cavity 14 is a bowl-shaped container, as is best shown in FIG. 2, and is intended to hold a pair of contact lenses for cleaning and disinfecting. It is covered by a removable screw-on cap 16. The cavity has a flat base 18 and to the underside of this is adhered one or more ultra-sonic transducers 20.

Figure 5:
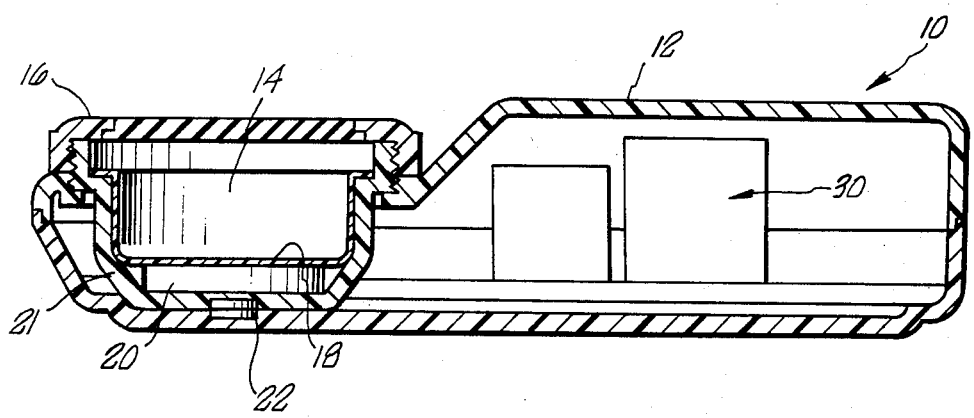
FIG. 5 is a section similar to FIG. 2 of a modified apparatus.

The housing 12 is of compact portable size such that it can conveniently be carried in a pocket. In an alternative embodiment shown in FIG. 5, however, the cavity and screw-on cap 16 can be removed as a unit from the rest of the housing 12. Thus, the cavity and transducer 20 are enclosed in an outer bowl portion 21 which slidably fits within a corresponding opening in the housing 12. It will be noted that the transducer or transducers 20 are also enclosed by this portion 21 for protection. To provide electrical connection to the transducer 20, an electrical connector 22 is provided. This has 3 female sockets on the underside of the portion 20 and 3 male projecting pins upstanding from the base 12a of the housing 12. When the cavity 14, and cap 16 are in position in the housing 12, these connect and provide the required electrical connection to the transducer or transducers.

The apparatus has its own power supply 23 in the form of dry batteries contained within the housing. A manually operated switch 24 for controlling operation is also provided together with an indicator light 26 to show when the apparatus is working.

Figure 3:
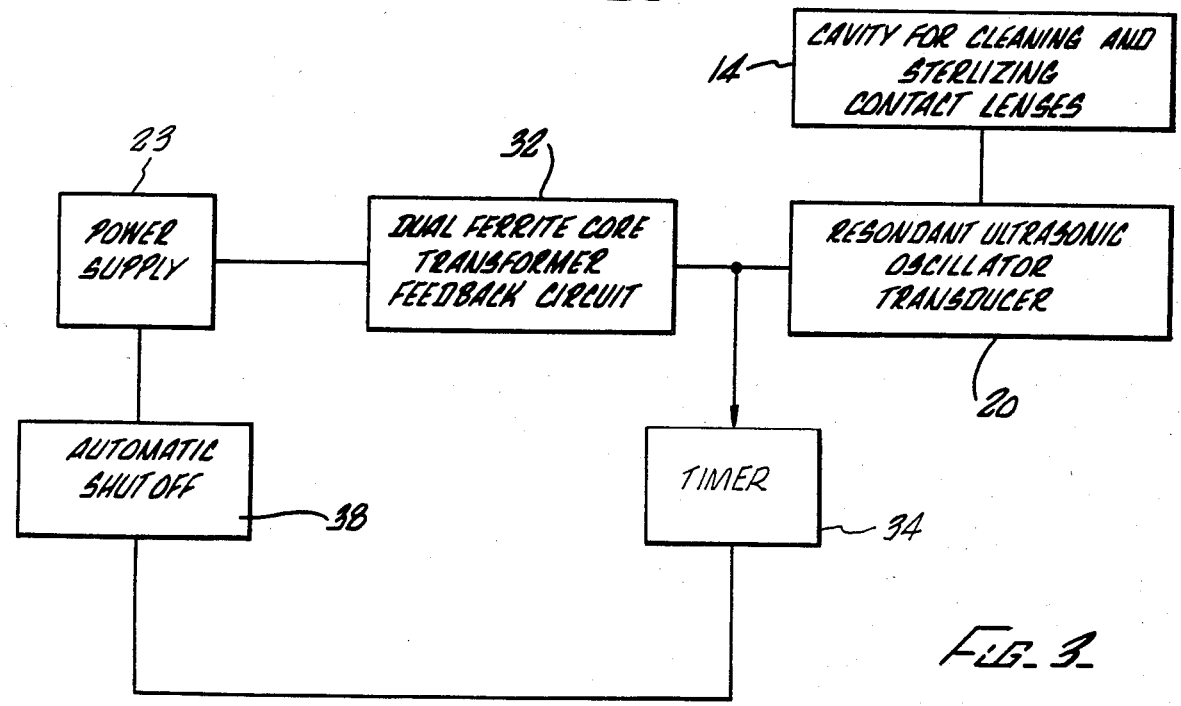
FIG. 3 is a block diagram illustrating the operation of the apparatus.
Figure 4:
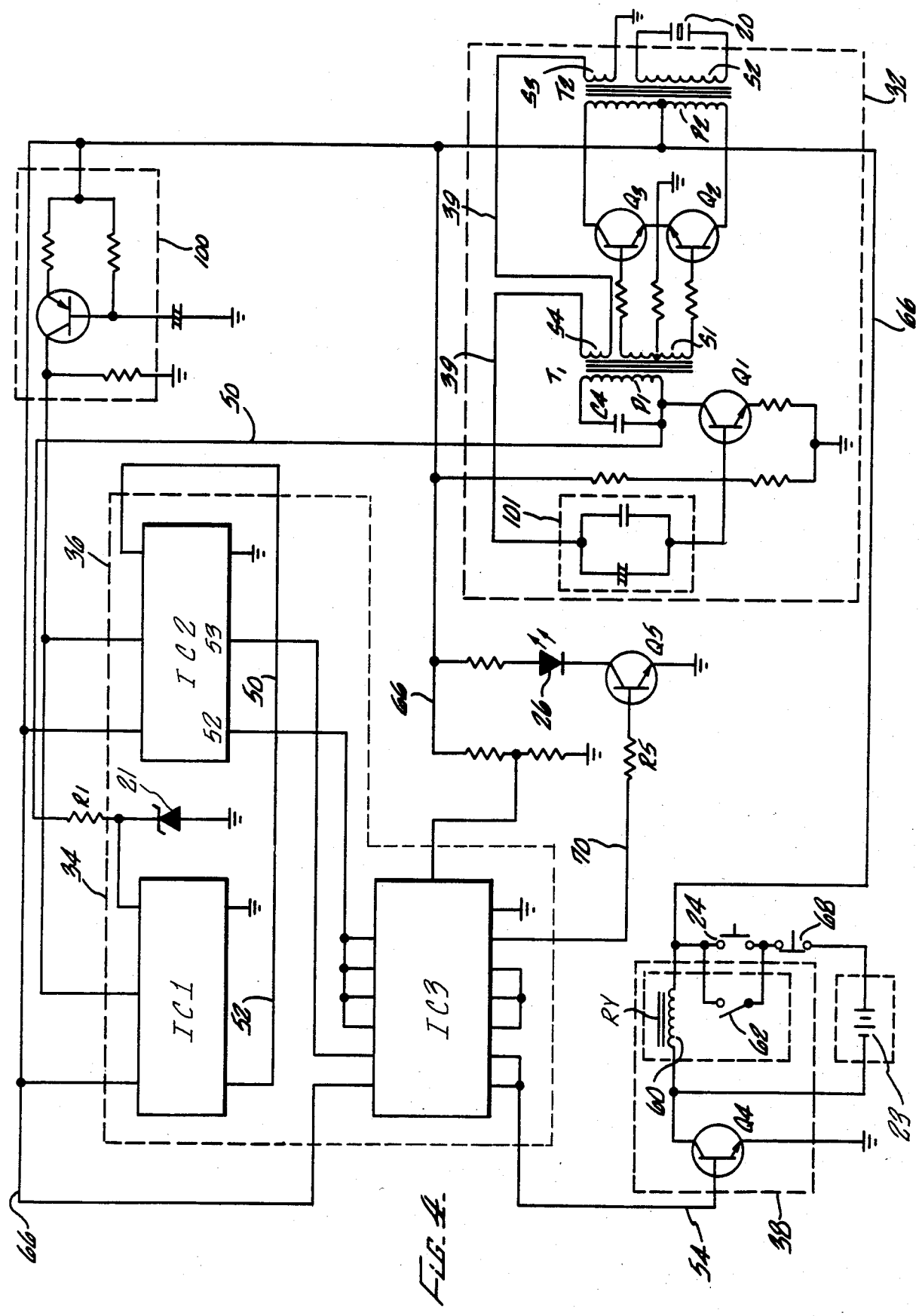
FIG. 4 is a circuit diagram of the electronic components in the apparatus.

In the housing, electronic circuitry 30 for operating the transducer is provided and that circuitry 30 is shown diagrammatically in FIG. 3 and in more detail in FIG. 4. The circuitry 30 includes a dual ferrite core transformer feedback oscillator circuit 32 whose output drives the transducer 20. Such a circuit is an example of a transformer feedback circuit using a core of high magnetic permeability and low core loss. An output is taken from the circuit 32 to a timer circuit 34. Thus, the timing of this circuit 34 is controlled by the oscillating frequency from the oscillator circuit. The timer in turn controls the operation of the circuit 32 by means of a shut-off switch 38 which controls the power supply 23. Preferably, the circuitry 30 operates at a frequency of 35 to 40 KHz.

Thus referring to FIG. 3, the user places contact lenses and saline solution in the cavity 14 and closes it with the cap 16. He then activates the circuit 32 and the ultrasonic vibrations supplied by the transducer 20 to the cavity clean and sterilize the lenses. The circuit 34 reaches a pre-set time and then the shut-off switch 38 disconnects the power supply 22 to the circuit 32 to terminate the operation and thereafter the user removes the cleaned lenses from the cavity 14.

As best shown in FIG. 4 the oscillator circuit 32 includes two ferrite cored transformers T1 and T2. An oscillating loop is formed by a capacitor C4 and the primary coil P1 of the transformer T1 and this is driven by transistor Q1. The output of the secondary coil S1 of the transformer is used in a push-pull amplifying circuit comprising the power transistors Q2 and Q3 to drive the primary coil P2 of the transformer T2. The secondary coil S2 of the transformer T2 in turn drives the transducer 20.

Feedback is supplied by secondary coils S3 and S4 of the transformers T1 and T2, respectively, along line 39 to the transistor Q1 to ensure that the whole circuit 32 oscillates resonantly and the coils S3 and S4 couple the two transformers together. Also, the resonant frequency is kept largely constant by this known arrangement irrespective of changes in the transducer 20. Thus the transducer will be affected by the amount of liquid placed in the cavity 14 and the size and type of contact lens and further by factors such as temperature and type of liquid. Despite this, the feedback in the circuit 32 ensures that the whole circuit remains in resonance and despite these changes the resonant frequency will only be insignificantly affected, usually by less than 500 Hz.

The circuit is also very efficient in its use of power and so an effective ultrasonic output to the cavity 14 can be provided by a power source 22 composed of dry batteries.

Because the oscillating frequency of the circuit 32 is substantially constant, it can be used to control the period of operation of the apparatus 10. Thus an output is taken along the line 50 from the oscillating loop formed by the capacitor C4 and the primary coil P1 of transformer T1 and that output is fed via resistor R1 to the counter circuit 34. This comprises integrated circuits IC1, IC2 and IC3. A zenner diode 21 limits the pulse height of the output.

The circuits IC1 and IC2 are counters which act as successive dividers of the oscillating pulses from the oscillator. There are sufficient dividing stages that after a pre-selected period of time, e.g. 9 minutes, the circuit IC2 will provide a changed output at pins 52 and 53 to the circuit IC3.

The circuit IC3 includes a logic gate and, when the circuit 30 is initially activated, the circuit IC3 provides an output along line 54, is applied to the base of a transistor Q4 which then conducts freely. As a result the relay coil 60 of a relay RY in series is activated. This has the effect of holding the switch contacts 62 of the relay RY closed so as to keep the overall circuit 30 activated from the power supply 22 via the positive line 66. When the circuit IC2 provides the changed output on pins 52 and 53, however, the output to circuit IC3 causes the latter to disable the transistor Q4 and as a result the switch contacts 64 open and the overall circuit 30 is disabled.

In parallel with the switch contacts 62 is provided the manually operated switch 24. As can be seen this has a relaxed off position. Thus when the user wishes to activate the apparatus, he closes that switch temporarily to by-pass the switch contacts 62 and activate the overall circuit 30 via the line 66. The oscillating circuit 32 begins and the timer circuit 34 is reset so that in turn the transistor Q4 becomes highly conductive. The switch contacts 62 of the relay RY therefore close and so when the user releases the switch 24 actuation of the circuit continues while the timer circuit 34 continues to count.

A cut-out safety switch 68 is provided in series with the switch 24 and acts as a safety measure.

A further output is taken from the circuit IC3 along a line 70, through resistor R5 to a transistor Q5 in series with a light emitting diode constituting the indicator light 26.

Figure 6:
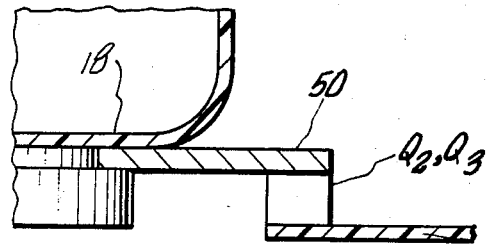
FIG. 6 is an enlarged detail section similar to FIG. 2 of a further modified apparatus.

According to a modified embodiment of the invention as shown in FIG. 6, the waste heat from the transistors Q2 and Q3 is used to heat the liquid in the cavity 14. This is achieved by a strip 50 of heat conducting metal attached to each transistor which bears against the underside of the flat base 16 of the cavity 14. In this way the waste heat is used to heat up the liquid in the cavity more quickly and so the time of operation can be reduced. This can be important if it is desirable to heat up the liquid to relatively high temperatures, e.g. 65° C. for 10 minutes. Simply to allow the internal heating of the fluid and lenses to reach this temperature as a result of the ultra-sonic energy may result in the lenses being degraded by too long in exposure to ultrasonic energy. Also the power transistors Q2 and Q3 give out a substantial amount of waste heat and this can be put to good use in this embodiment.

What is claimed is:

1. A contact lens cleaning and disinfecting apparatus, comprising at least one cavity for containing at least one contact lens together with an aqueous non-chemosterilant liquid, at least one ultrasonic transducer for applying ultrasonic vibrations to the liquid and lenses contained in the cavity, oscillating means for driving the ultrasonic transducer including a transformer feedback circuit using one or more cores of high magnetic permeability and low core loss to stabilize the resonant frequency of the ultrasonic transducer means, and a timer for controlling the energizing of the oscillator means for a predetermined period of time.

2. Apparatus as claimed in claim 1 in which the cavity has a cap to seal it and is itself removable together with the transducer from the housing of the apparatus so that lenses can be transported after cleaning and sterilizing or disinfecting and before use.

3. Apparatus as claimed in claim 1 or claim 2 in which the transformer feedback circuit is a dual ferrite core transformer feedback circuit.

4. Apparatus as claimed in claim 1 or claim 2 in which the timer is driven in its operation by receiving an input from the oscillating means.

5. Apparatus as claimed in claim 1 or claim 2 in which one or more power transistors are used in the feedback circuit that drives the transducer and heat conduction means are provided to transfer heat produced by the power transistors in operation to liquid in the cavity.

6. A contact lens cleaning and disinfecting apparatus, comprising at least one removable cavity for containing at least one contact lens together with an aqueous non-chemosterilant liquid, at least one ultrasonic transducer for applying ultrasonic vibrations to the liquid and lenses contained in the cavity, oscillating means for driving the ultrasonic transducer including a dual core transformer feedback circuit using cores of high magnetic permeability and low core loss to stabilize the resonant frequency of the ultrasonic transducer means, a timer driven in its operation by receiving its input from the oscillating means, one or more power transistors in the feedback circuit that drives the transducer, and heat conduction means to transfer the heat produced by the power transistors in operation to liquid in the cavity.

7. The contact lens cleaning and disinfecting apparatus according to claim 6 in which the heat conduction means comprises at least one strip of heat-conducting metal.

* * * * *